(12) United States Patent
Chang et al.

(10) Patent No.: US 7,751,040 B2
(45) Date of Patent: Jul. 6, 2010

(54) MICROCHIP WITH EXPANSION CHANNEL AND FLOWCYTOMETER USING THIS MICROCHIP

(75) Inventors: Jun-Keun Chang, Seoul (KR); Hyun-Woo Bang, Seoul (KR); Ho-Young Yun, Seoul (KR); Keun-Chang Cho, Seoul (KR); Chan-Il Chung, Gyeonggi (KR)

(73) Assignees: Digital Bio Technology Co., Ltd., Gwanak-Gu (KR); Seoul National University Industry Foundation, Seoul (KR)

( * ) Notice: Subject to any disclaimer, the term of this patent is extended or adjusted under 35 U.S.C. 154(b) by 263 days.

(21) Appl. No.: 12/089,016

(22) PCT Filed: Sep. 27, 2006

(86) PCT No.: PCT/KR2006/003835

§ 371 (c)(1),
(2), (4) Date: Apr. 2, 2008

(87) PCT Pub. No.: WO2007/040313

PCT Pub. Date: Apr. 12, 2007

(65) Prior Publication Data

US 2008/0218753 A1    Sep. 11, 2008

(30) Foreign Application Priority Data

Oct. 5, 2005    (KR) .................. 10-2005-0093500

(51) Int. Cl.
  *G01N 1/10*    (2006.01)
(52) U.S. Cl. ....................................... 356/246
(58) Field of Classification Search ......... 356/244–246, 356/334–342
  See application file for complete search history.

(56) References Cited

U.S. PATENT DOCUMENTS

| | | | |
|---|---|---|---|
| 6,537,501 B1 * | 3/2003 | Holl et al. ............... | 422/101 |
| 6,576,194 B1 * | 6/2003 | Holl et al. ............... | 422/81 |
| 2004/0163958 A1 * | 8/2004 | Kao et al. ............... | 204/450 |

* cited by examiner

*Primary Examiner*—Michael P Stafira
(74) *Attorney, Agent, or Firm*—Edwards Angell Palmer & Dodge LLP; Kongsik Kim

(57) ABSTRACT

Disclosed is a microchip for a flowcytometer. A channel is expanded around a point, on which laser beams emitted from an optical unit are focused, so that focused sample particles slow down when they pass the expanded portion. This improves the detection intensity of sample particles.

7 Claims, 5 Drawing Sheets

Fig. 8

| | | |
|---|---|---|
| $w_{sample} < d_{sample}$ | | $w_{eff} = 0$ (ideal) |
| $w_{sample} = d_{sample}$ | | $w_{eff} = 0$ (ideal) |
| $\Phi_\beta < w_{sample} < 2\, d_{sample}$ | | $w_{eff} = w_{sample} - d_{sample}$ |
| $w_{sample} = 1.5\, d_{sample}$ | | $w_{eff} = d_{sample}/2$ |
| $w_{sample} = 2\, d_{sample}$ | | $w_{eff} = d_{sample}$ |
| $w_{sample} > 2\, d_{sample}$ | | $w_{eff} = w_{sample} - d_{sample}$ |

MICROCHIP WITH EXPANSION CHANNEL AND FLOWCYTOMETER USING THIS MICROCHIP

TECHNICAL FIELD

The present invention relates to a flowcytometer, and more particularly to a channel design of a microchip having an expanded channel region in order to improve the sensitivity of sample detection inside a microchannel.

BACKGROUND ART

It is widely known in the field of microparticle analysis, e.g. flow cytometry, how to analyze cells while they are entrained by a sheath flow (i.e. buffer solution), and will now be described briefly.

When the sheath flow is disturbed, waterdrops are formed and absorb cells. Shortly before respective waterdrops escape from an adjacent portion of the flow, they are sorted out by detecting desired cells and applying electric fields to respective waterdrops. As a result, waterdrops containing desired cells are deflected by the electric fields and collected by a collection container. During this process, it is very crucial to know exactly when the waterdrops containing desired cells reach an electrified region in order to electrify specific waterdrops fully while other peripheral waterdrops are electrified slightly.

FIG. 1 shows a basic type of flow cytometry disclosed in U.S. Pat. No. 6,120,666. Referring to FIG. 1, microchannels are formed on a substrate (not shown) in a cross shape with a width small enough to allow cells 120 to pass through. The cross-shaped intersection of the microchannels acts as a focusing chamber 22, which is photographed by an image pickup device 160 (e.g. CCD camera). The resulting images are processed by an image control processor 150 so as to analyze the cells.

Particularly, a sample channel 100 extends upwards from the focusing chamber 22. Cells 120 (i.e. samples) flow in via the sample channel 100. A pair of focusing channels 102 and 104 is connected to both sides of the focusing chamber 22 so that sheath flows are introduced via them, respectively.

As shown in the drawing, a plurality of cells 120, which have been fed through the sample channel 100, are surrounded by sheath flows from both sheath flow channels 102 and 104. Then, the cells 120 pass through the focusing chamber 22 in a series so that they are photographed by the image pickup device 160 and analyzed by the image control processor 150.

The stream of the cells 120 and the sheath flows is controlled by the difference in electric potential among respective channels 100, 102, 104, and 106, which is created by applying electric fields to them.

However, the above-mentioned conventional flow cytometer, which uses electric fields so as to control cells and sheath flows, has the following problems.

The equipment necessary to apply electric fields is expensive and increases the price of the cytometer.

Since the buffer solution used as the sheath flow must be directed by electric fields, the buffer solution must be made of a conductive material. This extremely narrows the range of selectable buffer solutions.

Movement of the sheath flow based on the difference in electric potential is too slow. This lengthens the analysis time. In order to avoid this, strong electric fields of kV grade must be applied to respective channels so as to increase the difference in electric potential. However, strong electric fields unfavorably separate a specific substance (e.g. protein) from the cells. Consequently, the strength of electric fields is still limited, and the problem of slow sheath flow remains unsolved.

When microparticles have missing portions, particularly deformed red blood corpuscles, or when microparticles flow while being slanted, the scanning means (i.e. laser) is likely to pass through the missing portions or vacancies resulting from the slant. In other words, the image pickup device may fail to recognize the microparticles.

In an attempt to solve the problems occurring in the conventional flowcytometer based on electric field application, inventors of the present invention have proposed an improved apparatus as disclosed in Registered Korean Patent No. 473, 362 entitled "APPARATUS AND METHOD FOR MICROPARTICLE ANALYSIS", which will now be described with reference to FIG. 2.

As shown in FIG. 2, the apparatus includes a substrate having a focusing chamber formed thereon. At least one sample channel is formed on the substrate so as to introduce samples, particularly microparticles (e.g. cells) into the focusing chamber. At least one sheath flow channel is formed on the substrate so as to introduce a sheath flow into the focusing chamber. The sheath flow surrounds the samples and directs them in a series inside the focusing chamber. Each of the sample channel, sheath flow channel, and sorting channel is provided with a pressure control means for establishing pressure gradients with respect to other channels. The resulting pressure gradients direct the samples and the sheath flow into the focusing and shorting channels from respective channels.

Each pressure control means includes a vacuum pump connected to each container, a microvalve positioned between the vacuum pump and the container, a pressure sensor for sensing the pressure within the container, and a pressure controller for controlling the operation of the microvalve in accordance with signals from the pressure sensor.

As the samples are entrained by the sheath flow and travel in a series inside the focusing chamber due to the pressure gradients created by the pressure control means, an image pickup means photographs the samples. The resulting images are transmitted to an image controller, which counts and analyzes the samples moving inside the focusing chamber. The image controller recognizes the type of the samples and transmits corresponding information to the pressure controller for the sorting channel. As a result, the samples are sorted out according to type by corresponding pressure controllers as they pass through respective sorting channels.

As such, the improved apparatus utilizes pressure gradients instead of the difference in electric potential. Consequently, the flow rate of the sheath flow can be increased substantially without limiting the range of selectable buffer solutions. This reduces the manufacturing cost. Furthermore, there is no cell separation resulting from strong electric fields, and the reliability of cell analysis is improved remarkably. It is also possible to correctly recognize deformed microparticles, which have missing portions, and prevent microparticles from flowing while being slanted.

However, although the flowcytometer based on pressure gradients has a higher throughput due to the increased flow rate of samples and sheath flows, signals detected by detectors are too weak to guarantee an accurate sample analysis, because cells move too fast at the channel point, on which laser beams from optical units are focused, to generate a sufficient amount of fluorescence or scattering. Particularly, samples having weak fluorescence cannot be detected at all. This fatally degrades the performance of the analysis apparatus.

This problem may be avoided if the pressure of sheath flows is adjusted to slow down samples and sheath flows. This, however, substantially reduces the throughput. Although the quality of sample detection may be improved by using an optical structure having a very high resolution, the higher the resolution is, the more expensive the apparatus becomes. Furthermore, improvement of the resolution of the optical structure has its own limits.

Therefore, the present invention has been made in view of the above-mentioned problems, and it is an object of the present invention to provide a flowcytometer capable of detecting samples accurately even when samples and sheath flows have a high flow rate so that the quality of sample detection can be improved with no decrease in throughput.

Another object of the present invention is to provide a flowcytometer adapted to increase the resolution for sample detection if the flow rate of samples and sheath flows increases, in order to guarantee accurate sample detection regardless of the flow rate and improve the throughput.

These objects of the present invention are accomplished by expanding a portion of a focusing channel, in which samples and sheath flows combine and flow, around a channel point, on which laser beams are focused, so that sample particles slow down only in the expanded channel, thereby improving the detection intensity of sample particles. Particularly, a microchip for a flowcytometer according to the present invention has a channel expanded around a channel point, on which laser beams from optical units are focused, so that focused sample particles slow down only near the expanded channel while remaining in a focused condition. This improves the detection intensity of sample particles.

As such, the entire sample analysis throughput remains constant, because the overall flow rate of sample particles does not decrease. In addition, accurate sample analysis is guaranteed, because the sample particles slow down only in the expanded channel.

According to an aspect of the present invention, there is provided a microchip used in a flowcytometer for analyzing samples, the samples being microparticles flowing through a microchannel formed on a substrate, the microchip including a sample channel, samples flowing through the sample channel; a sheath flow channel, a sheath flow flowing through the sheath flow channel; a focusing channel, focused sample particles flowing through the focusing channel, the focused sample particles being a combination of the samples and the sheath flow; and an expanded channel formed by expanding a portion of the focusing channel, the portion being around a point for sample analysis.

According to another aspect of the present invention, there is provided a flowcytometer for analyzing samples, the samples being microparticles flowing through a microchannel, the apparatus including a focusing chamber formed on a substrate; a sample channel connected to the focusing chamber; at least one sheath flow channel connected to the focusing chamber so as to introduce a sheath flow, the sheath flow surrounding samples so that the samples flow in a series, the samples having been introduced into the focusing chamber via the sample channel; a focusing channel, focused sample particles passing through the focusing channel, the focused sample particles being a combination of the samples and the sheath flow; a pressure control means for establishing a pressure gradient between respective channels so that the samples and the sheath flow are directed to respective sorting channels via the focusing channel; and a signal detection device for detecting signals generated from samples, laser beams emitted from an optical unit being focused on the samples, wherein a portion of the focusing channel is expanded, the portion being around a point, the laser beams emitted from the optical unit being focused on the point, so that, when focused sample particles pass the expanded portion of the focusing channel, the focused sample particles slow down while remaining in a focused condition and sample particle detection intensity is improved.

The inventors of the present invention have made the following discovery: when particles have been focused into a fluid, an increase in width of a channel, through which the fluid passes, reduces the flow rate of the fluid and enlarges the width thereof. In the case of particles within the fluid, their flow rate decreases in the same manner as the fluid, but they continue to flow without being disturbed (i.e. they remain focused). Based on this discovery, it has been proposed to expand only a portion of the focusing channel so that particles slow down only in the expanded section while remaining focused. The resulting microchip for a flowcytometer can both increase the sample analysis throughput and improve the sample analysis quality.

BRIEF DESCRIPTION OF THE DRAWINGS

The foregoing and other objects, features and advantages of the present invention will become more apparent from the following detailed description when taken in conjunction with the accompanying drawings in which:

FIG. 8 shows examples of an effective focusing sample flow width under various conditions regarding the width of sample flows and the diameter of sample particles.

MODE FOR THE INVENTION

Reference will now be made in detail to the preferred embodiments of the present invention.

Prior to detailed description of the present invention, relevant terminologies will be clarified for better understanding of the invention: "sample solution" implies that it has not yet been combined with a sheath flow, and "sample flow" refers to a focused sample solution after a sample solution is combined with a sheath flow.

Figure 1:
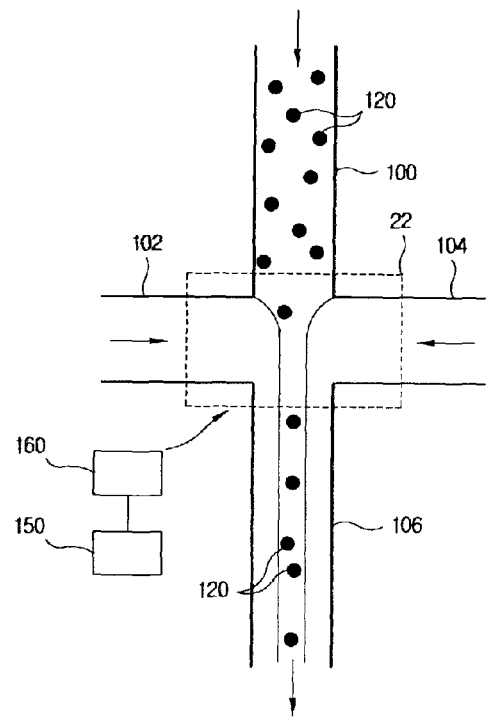
FIG. 1 shows the construction of a conventional flowcytometer.
Figure 2:
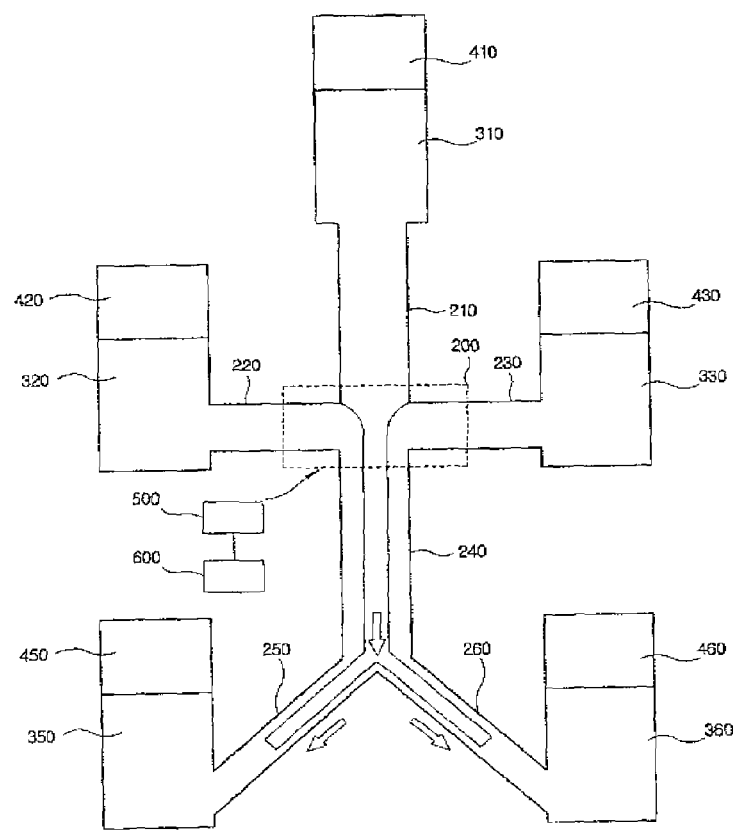
FIG. 2 shows the construction of a conventional flowcytometer.
Figure 3:
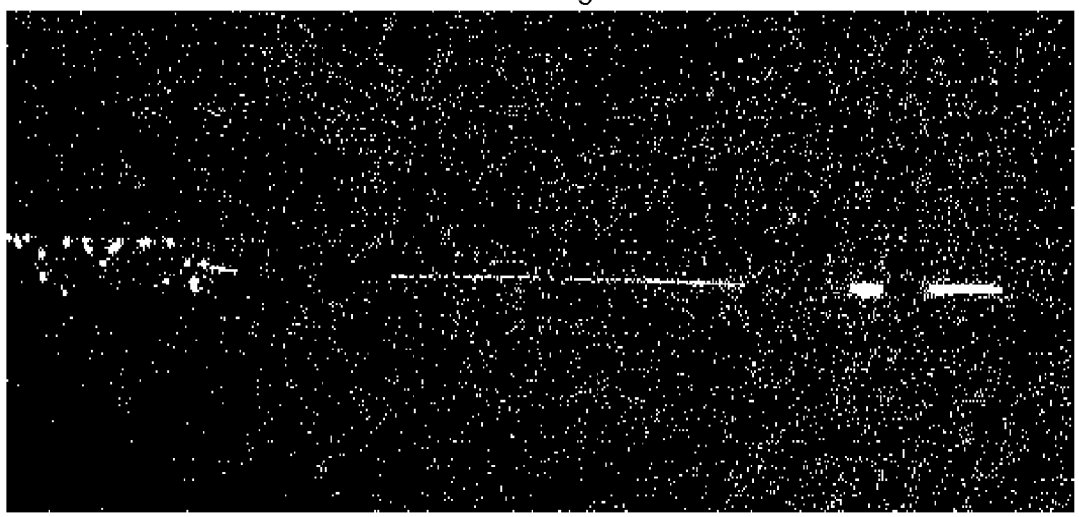
FIG. 3 shows signal intensities observed at a number of locations in a microchip having an expanded channel according to the present invention.

FIG. 3 shows a microchip having an expanded channel according to the present invention. Particularly, FIG. 3 shows a varying detection intensity of sample particles at a number of locations in a focusing channel, a normal channel, and an expanded channel while the sample particles pass through the expanded channel from the focusing channel. According to the prior art, the channel has a constant width from a portion downstream of the focusing channel, at which a sample solution is combined with a sheath flow. According to the present invention, as shown in FIG. 3, the channel has an expanded portion, which is illuminated for sample detection. As a result, the flow rate drops only around the expanded channel point, on which sample particles are focused. This improves the signal intensity of sample detection.

Such an improvement in sample detection intensity resulting from the characteristic structure according to the present invention can be easily observed from FIG. 3. It is clear from FIG. 3 that the detection intensity of fluorescent sample particles is weak in the normal channel (i.e. which is not expanded) downstream of the channel where a sample solution is combined with a sheath flow, but the intensity is much stronger in the expanded channel. As such, a microchip designed according to the present invention has the advantage of improved detection intensity of sample particles, because the sample solution has a lower flow rate in the expanded channel than in the normal channel.

Figure 4:
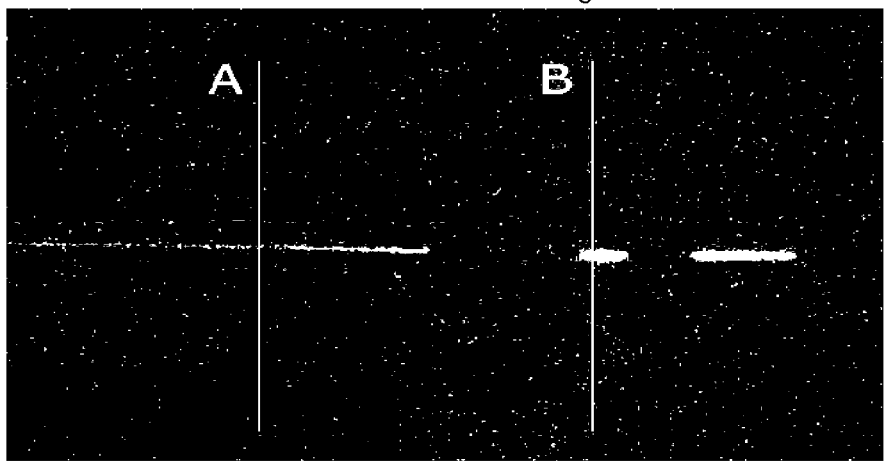
FIGS. 4 and 5 show signal intensities and coefficients of variation measured when fluorescent sample particles pass through an expanded channel and a normal channel of a microchip having an expanded channel, respectively.
Figure 5:
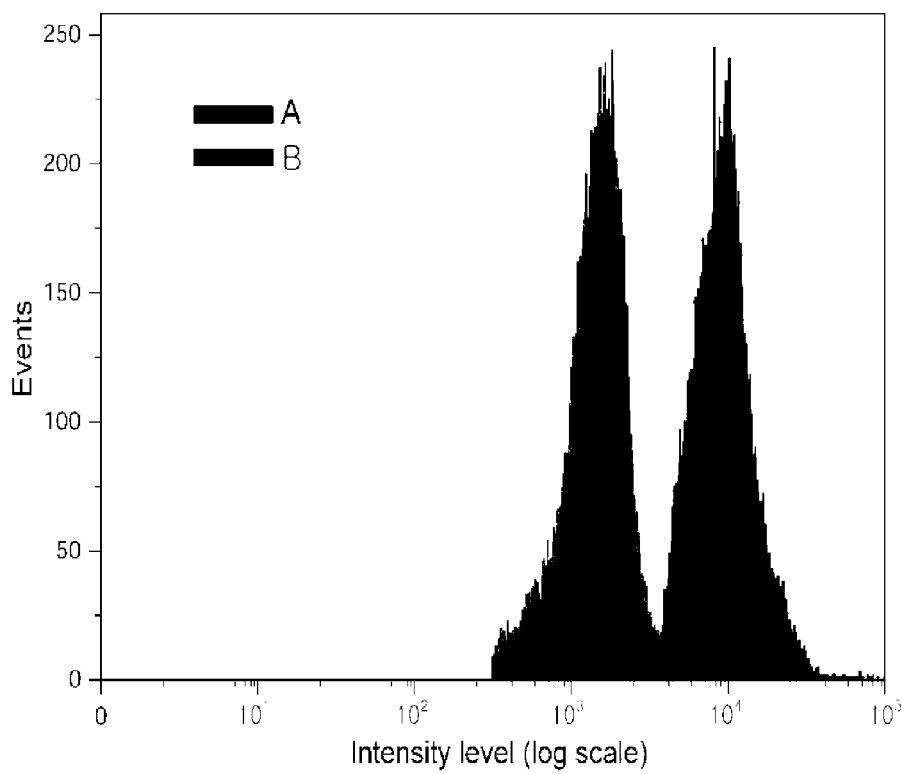

FIG. 4 shows signal intensities when fluorescent sample particles pass through an expanded channel (region B) and a normal channel (region A) as in the case of FIG. 3, although the expanded channel has a different shape from that shown in FIG. 3. FIG. 5 shows signal intensities measured in the normal channel (region A) and the expanded channel (region B) shown in FIG. 4, together with a difference in coefficients of variation. Data shown in FIGS. 4 and 5 is based on observation of fluorescent signals when 3 μm polyurethane microbeads available from Polysciences, Inc., Warrington, Pa., USA, are used. The result shows the same detection throughput for both normal and expanded channels (about 1,500 particle/second). As in the case of FIG. 3, the signal intensity in the expanded channel is about ten times larger than that in the normal channel. In addition, the coefficient of variation for signal intensities in the expanded channel is about 20% lower than that in the normal channel. (Based on measurements shown in FIG. 5, the average coefficient of variation for the normal channel is 1.8%, and that for the expanded channel is 1.4%.) This demonstrates that the intensity and purity of signals detected in the expanded channel can be improved with no decrease in the detection throughput.

Figure 6:
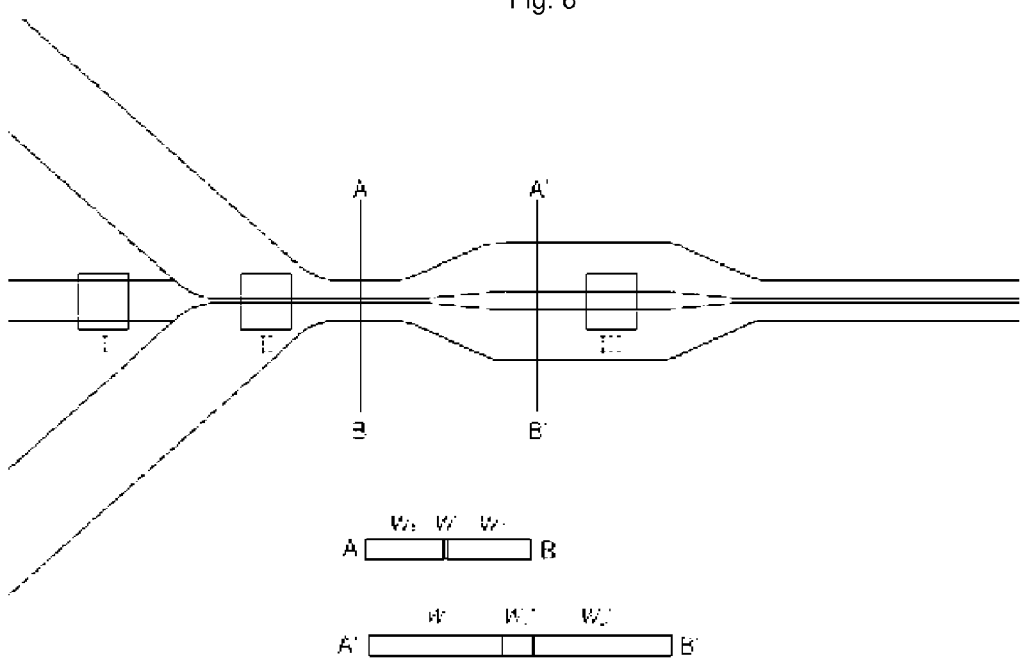
FIGS. 6 and 7 show in detail the width and size of sample particles and sample flows in a microchip having an expanded channel according to the present invention, as well as at a number of locations therein, respectively.
Figure 7:
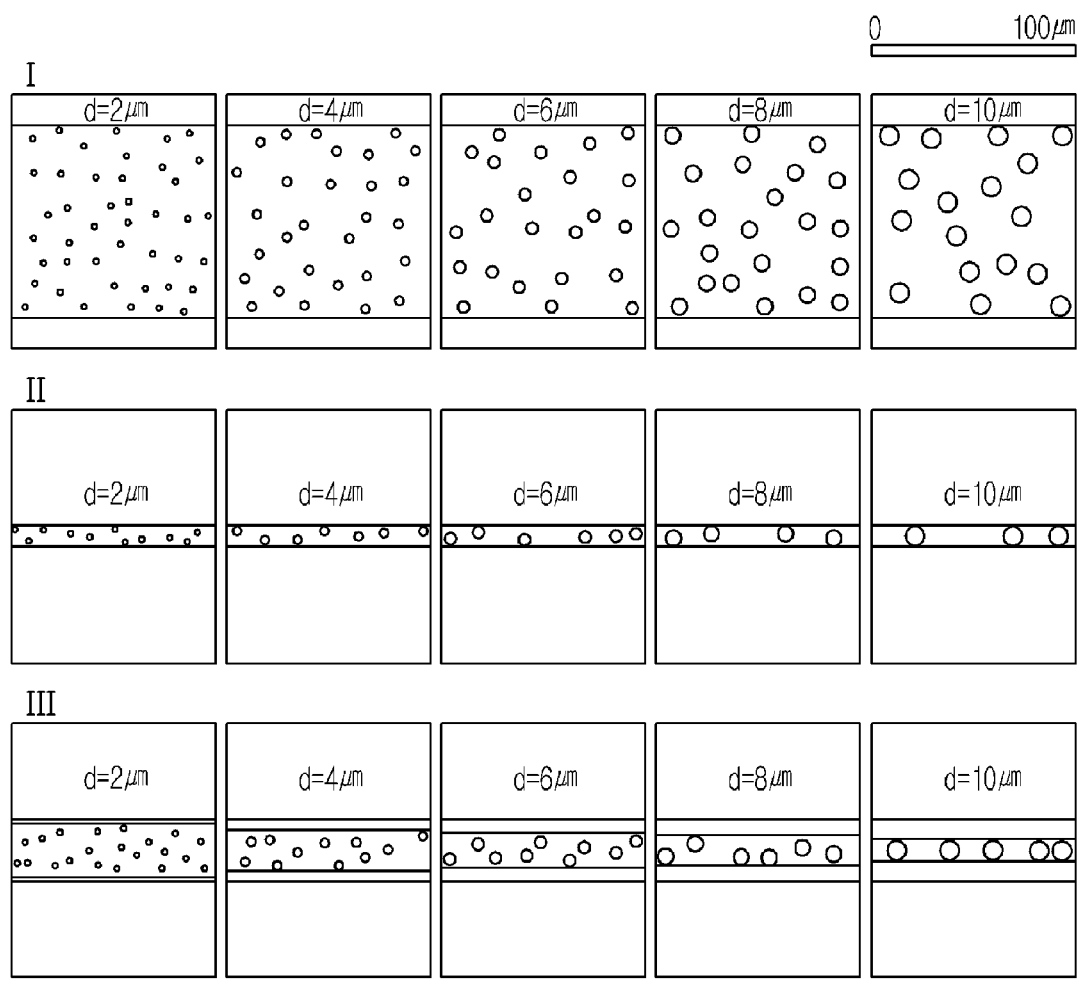

FIGS. 6 and 7 show in detail the width of sample flows with regard to the size of sample particles in a focusing channel, a normal channel, and an expanded channel of a microchip having an expanded channel according to the present invention. It is clear from FIGS. 6 and 7 that, in the case of a microchip designed according to the present invention, the sample flow in the expanded channel is much slower than that in the normal channel.

This is obvious from observation of sample particles photographed in respective regions, as clearly shown in FIG. 7. In FIG. 6, a sample solution before combination with a sheath flow is labeled region I, a sample flow after combination with a sheath flow is labeled region II, and a sample flow in an expanded channel is labeled region III. In FIG. 6, for example, $W_1+W_2+W_3=100$ μm, $W_2=10$ μm, $W'_1+W'_2+W'_3=300$ μm, and $W'_2=30$ μm.

As shown in region III of FIG. 7, there occurs a discrepancy between the path of sample particles and the streamline of a sample flow surrounding them when the sample particles and the same flow pass through the expanded region. It has been discovered that the discrepancy increases in proportion to the size of sample particles. Particularly, when the diameter d of sample particles is 2 μm in region III of FIG. 7, there is little difference in width between the path of the sample particles and the sample flow surrounding them. However, when the diameter d is 10 μm, the width of the path of the sample particles is the same as the diameter of the sample particles, while the width of the sample flow remains unchanged. As a result, there is a large difference in width between the path of the sample particles and the sample flow.

The sample particles tend to remain focused even after passing through the expanded channel region, unlike the adjoining liquid. For example, when the width of a focused sample flow increases from 10 μm to 100 μm, the streamline of the sample flow increases by a factor of 10, but the sample particles inside the sample flow remain on the central line (with the same diameter of 10 μm). This is because the effect of particle size increases substantially when the particle diameter approaches the width of the focused sample flow. When the sample particles pass through the expanded channel region, their lateral velocity decreases. This means that the velocity of the focused sample particles can be reduced locally with no departure of the sample particles from the central line of the flow. The resulting particle stream in the expanded channel region consists of dense, focused, and slow particles (e.g. particles of diameter d=10 ∞m shown in FIG. 7) arranged along a line.

In order to improve the detection intensity of sample particles by expanding the channel, much emphasis needs to be placed on the relationship among the width and depth of the sheath flow and the sample channel, the size of the sample particles, the ratio of channel expansion, and the diameter of the detection spot.

As mentioned above, the effect of sample particle size increases substantially when the diameter of the particles approaches the width of the focused sample flow. Therefore, when an expanded channel is used, the concept of "effective focusing sample flow width" $W_{eff}$ becomes necessary, as defined by equation (1) below.

$$W_{eff}=W_{sample}-d_{sample} \quad (1)$$

Wherein, $W_{sample}$ refers to the width of the sample flow before the expansion, and $d_{sample}$ refers to the diameter of the sample particles.

As is obvious from equation (1), the effective focusing sample flow width $W_{eff}$ is obtained by subtracting the diameter of the sample particles from the width of the sample flow. FIG. 8 shows examples of the effective focusing sample flow width under various conditions regarding the width of sample flows and the diameter of sample particles.

When the width of a sample flow has increased in an expanded channel region, the resulting sample flow width $W_{final}$ is obtained by multiplying an effective focusing sample flow width before the expansion by an expansion ratio α, as defined by equation (2) below.

$$W_{final}=\alpha \times W_{eff} \quad (2)$$

Preferably, the size of the portion illuminated with laser beams is equal to or larger than the sum of the sample flow width $W_{final}$ and the particle diameter $d_{sample}$. Particularly, the following condition is preferably satisfied for measurement of sample particle signals.

$$W_{final}+d_{sample} \leq W_{beam} \quad (3)$$

Wherein, $W_{beam}$ refers to the diameter of a detection spot.

In other words, there is no problem with the sensitivity for signal detection if equation (3) is satisfied. If the width of a focused sample flow is smaller than the size of sample particles as shown in FIG. 8, i.e. if the effective focusing sample flow width $W_{eff}$ is 0, equation (3) is automatically satisfied in theory, even when the channel is expanded infinitely (α=∞), because, in equation (2), $W_{final}=0$ (in general, since the diameter of a detection spot of laser beams is larger than the particle diameter, $d_{sample} \leq W_{beam}$).

A flowcytometer according to the present invention includes a signal detection device for analyzing samples. An image pickup means may be used as the signal detection device. The signal detection device may also be a photomultiplier tube for detecting fluorescent signals emitted from samples or a photodiode for detecting scatter signals.

As can be seen from the foregoing, according to the present invention, it is possible to detect samples accurately even when samples and sheath flows move fast so that the quality of sample detection can be improved with no decrease in detection throughput.

In addition, even when the current flow rate of samples and sheath flows rises, accurate sample detection is guaranteed by increased sample detection resolution. This improves the detection throughput.

While this invention has been described in connection with what is presently considered to be the most practical and preferred embodiment, it is to be understood that the invention is not limited to the disclosed embodiment and the drawings, but, on the contrary, it is intended to cover various modifications and variations within the spirit and scope of the appended claims.

The invention claimed is:

1. A microchip used in a flowcytometer for analyzing samples, the samples being microparticles flowing through a microchannel formed on a substrate, the microchip comprising:
  a sample channel, samples flowing through the sample channel;
  a sheath flow channel, a sheath flow flowing through the sheath flow channel;
  a focusing channel, focused sample particles flowing through the focusing channel, the focused sample particles being a combination of the samples and the sheath flow; and
  an expanded channel formed by expanding a portion of the focusing channel, the portion being around a point for sample analysis.

2. The microchip as claimed in claim 1, wherein the expanded channel has an enlargement width defined by equations $$W_{eff} = W_{sample} - d_{sample} \quad (1)$$

$$W_{final} = \alpha \times W_{eff} \quad (2)$$

$$W_{final} + d_{sample} \leq W_{beam} \quad (3)$$

wherein, $W_{eff}$ refers to an effective focusing sample flow width, $d_{sample}$ refers to a sample particle diameter, $W_{final}$ refers to a sample flow width when a width of a sample flow has increased in an expanded channel region, $\alpha$ refers to an enlargement ratio, and $W_{beam}$ refers to a detection spot diameter.

3. The microchip as claimed in claim 1 or 2, wherein laser beams emitted from an optical unit of the flowcytometer are focused into the expanded channel.

4. The microchip as claimed in claim 1 or 2, wherein the flowcytometer comprises a signal detection device, the signal detection device comprising an image pickup means, a photomultiplier tube, or a photodiode.

5. A flowcytometer for analyzing samples, the samples being microparticles flowing through a microchannel, the apparatus comprising:
  a focusing chamber formed on a substrate;
  a sample channel connected to the focusing chamber;
  at least one sheath flow channel connected to the focusing chamber so as to introduce a sheath flow, the sheath flow surrounding samples so that the samples flow in a series, the samples having been introduced into the focusing chamber via the sample channel;
  a focusing channel, focused sample particles passing through the focusing channel, the focused sample particles being a combination of the samples and the sheath flow;
  a pressure control means for establishing a pressure gradient between respective channels so that the samples and the sheath flow are directed to respective sorting channels via the focusing channel; and
  a signal detection device for detecting signals generated from samples, laser beams emitted from an optical unit being focused on the samples, wherein a portion of the focusing channel is expanded, the portion being around a point, the laser beams emitted from the optical unit being focused on the point, so that, when focused sample particles pass the expanded portion of the focusing channel, the focused sample particles slow down while remaining in a focused condition and sample particle detection intensity is improved.

6. The flowcytometer as claimed in claim 5, wherein the expanded portion of the focusing channel has an enlargement width defined by equations $$W_{eff} = W_{sample} - d_{sample} \quad (1)$$

$$W_{final} = \alpha \times W_{eff} \quad (2)$$

$$W_{final} + d_{sample} \leq W_{beam} \quad (3)$$

wherein, $W_{eff}$ refers to an effective focusing sample flow width, $d_{sample}$ refers to a sample particle diameter, $W_{final}$ refers to a sample flow width when a width of a sample flow has increased in an expanded channel region, $\alpha$ refers to an enlargement ratio, and $W_{beam}$ refers to a detection spot diameter.

7. The flowcytometer as claimed in claim 5 or 6, wherein the signal detection device comprises an image pickup means, a photomultiplier tube, or a photodiode.

* * * * *